United States Patent [19]

Tanaka et al.

[11] Patent Number: 5,331,169
[45] Date of Patent: Jul. 19, 1994

[54] SURFACE INSPECTION METHOD AND DEVICE WITH IRRADIATION

[75] Inventors: Kazumoto Tanaka, Hiroshima; Kazuo Hironaka, Hatsukaichi; Yoshimi Shimbara, Hiroshima, all of Japan

[73] Assignee: Mazda Motor Corporation, Hiroshima, Japan

[21] Appl. No.: 981,443

[22] Filed: Nov. 25, 1992

[30] Foreign Application Priority Data

Nov. 25, 1991 [JP] Japan .................... 3-309148

[51] Int. Cl.5 .................... G01N 21/88; G01N 21/55; G01B 11/30
[52] U.S. Cl. .................... 250/372; 250/358.1; 356/237
[58] Field of Search .................... 250/372, 358.1, 572; 356/237, 446, 445

[56] References Cited

U.S. PATENT DOCUMENTS

| 4,629,319 | 12/1986 | Clarke et al. ................. 356/237 |
| 5,041,726 | 8/1991 | Chang et al. ............. 250/358.1 X |
| 5,072,128 | 12/1991 | Hayano et al. . | |
| 5,153,445 | 10/1992 | Stapleton .................. 356/237 X |
| 5,208,766 | 5/1993 | Chang et al. ............... 356/445 X |

FOREIGN PATENT DOCUMENTS

62-233710 10/1987 Japan .

Primary Examiner—Constantine Hannaher
Assistant Examiner—Edward J. Glick
Attorney, Agent, or Firm—Keck, Mahin & Cate

[57] ABSTRACT

An inspection method including the steps of irradiating a light with a predetermined changing pattern onto a substantially specular surface to be inspected through an irradiation device facing the surface, forming an image based on reflected light in correspondence with the predetermined changing pattern by an imaging device, and utilizing reflected light of only 200-350 nm wavelength to form the image so as to detect a flaw in the surface by identifying points which differ from the changing pattern of the irradiation device. The flaws in the coating can be detected with a high accuracy irrespective of the color of the coating surface. An inspection device is also provided for the same object.

5 Claims, 10 Drawing Sheets

SURFACE INSPECTION METHOD AND DEVICE WITH IRRADIATION

CROSS-REFERENCE TO RELATED APPLICATION

The present invention relates to U.S. patent application Ser. No. 723,174, filed on Jun. 28, 1991, entitled "SURFACE DEFECT INSPECTION APPARATUS", which is assigned to the same assignee as the present invention.

BACKGROUND OF THE INVENTION

1. Field of the Invention

The present invention relates to a surface inspection method and device of a vehicle body surface with a coating.

2. Description of Related Art

Conventionally, as a technique for inspecting the vehicle body surface for coating flaws, it has been known to have an imaging device, such as a video camera, receive a specular reflection light which is irradiated on the coating surface by means of a light irradiation device so as to form an image. A processing device then processes the image to detect flaws (for example, see Japanese Patent Public Disclosure No. 62-233710). This is because the coating surface can be treated as a smooth specular surface. In this case, generally, visible light with a wavelength of 380-780 nm is used as the irradiation light.

In U.S. Pat. No. 5,072,128, another type of inspection device is disclosed.

However, the conventional way of inspecting the coating surface is disadvantageous in that the formed image loses clarity when a specific color of the coating, such as a white base coating, is used. As a result, it is difficult to detect flaws in the coating with a desirable quality.

SUMMARY OF THE INVENTION

It is therefore an object of the present invention to provide an inspection method for inspecting a coating surface by utilizing irradiation which can detect the flaws in the coating accurately irrespective of the color of the coating.

It is another object of the present invention to provide an inspection device which can detect the flaws in the coating surface.

The above object can be accomplished by an inspection method, according to the present invention, comprising the steps of irradiating a light with a predetermined changing pattern onto a specular surface to be inspected through an irradiation device facing the surface, forming an image based on reflected light in correspondence with the predetermined changing pattern by means of an imaging device, and utilizing reflected light of only 200-350 nm wavelength to form the image so as to detect a flaw of the surface by identifying points which differ from the changing pattern of the irradiation device.

In another aspect of the invention, an inspection device according to the present invention is provided. The inspection device comprises means for irradiating a light onto a surface to be inspected, image forming means for forming an image of the irradiation means based on reflected light and image processing means for utilizing the reflected light within a wavelength of 220-350 nm to detect a flaw on the surface based on the image.

In a preferred embodiment, the irradiation means irradiates light having a wavelength of 220 nm-350 nm onto the surface.

In another embodiment of the present invention, the image forming means only receives light having a wavelength of 220 nm-350 nm.

When an inspection light is irradiated onto a surface with a coating, the specular reflection occurs on the surface of the coating because the surface of the coating is substantially specular. However, the coating layer includes fine particles of various pigments as coloring material which is included in a paint as a coating material. As a result, when the light is irradiated onto the surface to be inspected, a diffused reflection, as well as the specular reflection, occurs because the irradiated light is reflected on the surface of the fine particles of the pigments in the various directions. Consequently, when all of the reflection light is introduced to a camera for forming an image, not only the specular reflection light but also the diffused reflection light is introduced to the camera. The diffused reflection light to be kept away from forming the image of the coating surface is undesirably included so as to be processed. As a result, the image becomes blunt and makes proper detection of the flaw difficult when the flaw of the surface is detected based on the change of the image formed by the specular reflection light.

The inventors of the present invention studied optical characteristics such as a transmission or absorption of the pigments included in the paint. Generally, a white paint includes only a titanium oxide as a pigment. As a carbon black is mixed with titanium oxide, the color of the paint becomes dark. If only the carbon black is included in the paint, a black paint is obtained. It is well-known that the titanium oxide exhibits a high transmission characteristic while the carbon black exhibits a low transmission characteristic or high absorption characteristic. A white coating including the titanium oxide has a tendency to produce a diffused reflection while a black coating including the carbon black has less of a tendency to produce the diffused reflection.

According to the present invention, the imaging means forms the image by utilizing only the specular reflection light and excluding the diffused reflection light so that the condition of the coating surface can be assessed with a high clarity by the image processing means. As a result, flaws on the coating surface can be easily detected so that the judgement can be easily and accurately made as to whether or not the coating surface meets with a requirement for a desired quality level.

The above and other features of the present invention will be apparent from the detailed description and by making reference to the accompanying drawings.

DESCRIPTION OF THE PREFERRED EMBODIMENTS

The inventors of the present invention tested the reflection rate of three coatings which are formed by different compositions of paint.

Sample 1 . . . A coating including only titanium oxide as a pigment.

Sample 2 . . . A coating including a mixture of titanium oxide and carbon black at a predetermined ratio as a pigment.

Sample 3 . . . A coating including only carbon black as a pigment.

A light is irradiated onto the coating surfaces of the respective paints. The reflection rate of the irradiation is measured as the wavelength of the irradiation light is changed continuously. In this case, the rates of the specular and diffused reflections are measured separately. The results are shown in FIGS. 1, 2 and 3 with regard to sample 1, in FIGS. 4, 5 and 6 with regard to sample 2 and in FIGS. 7 and 8 with regard to sample 3.

Figure 1:
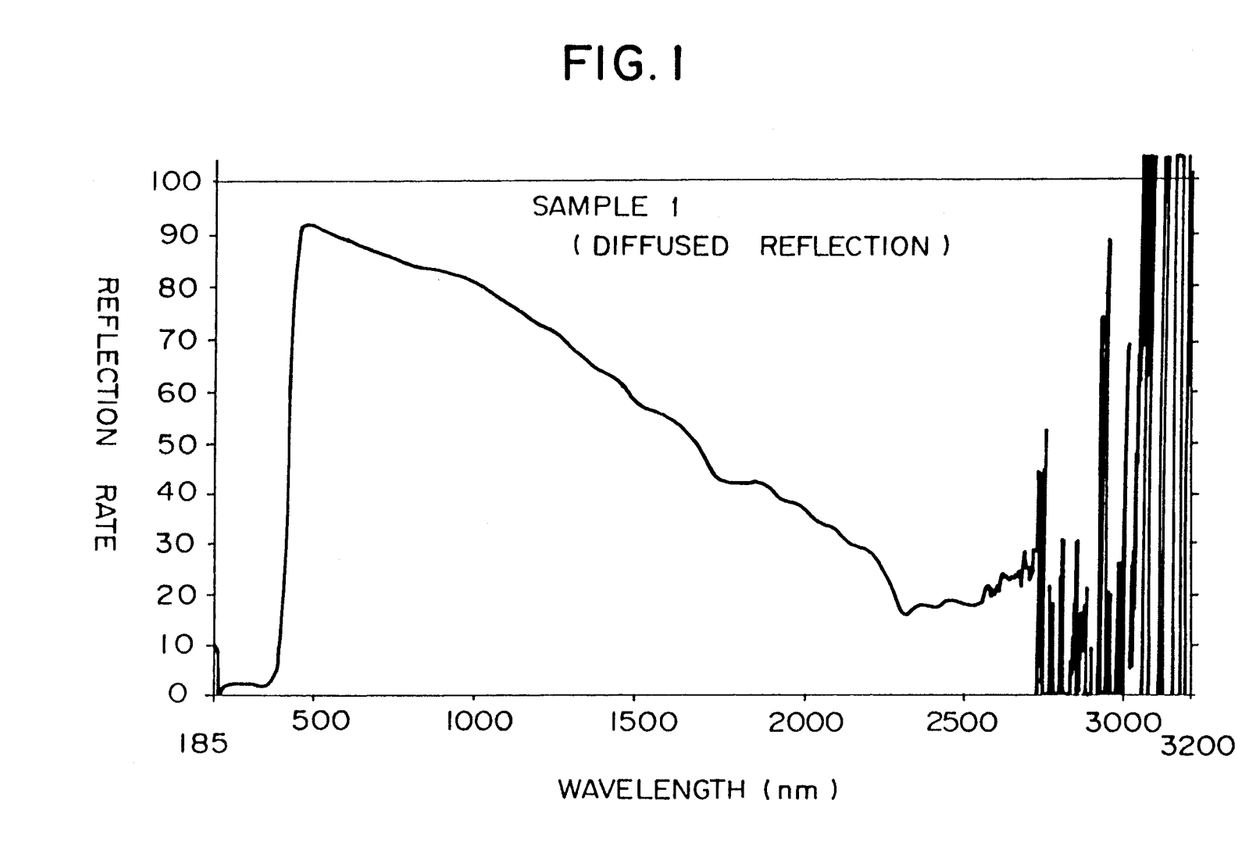
FIGS. 1-8 are graphical representations showing relationships between the reflection rate and wavelength.
Figure 2:
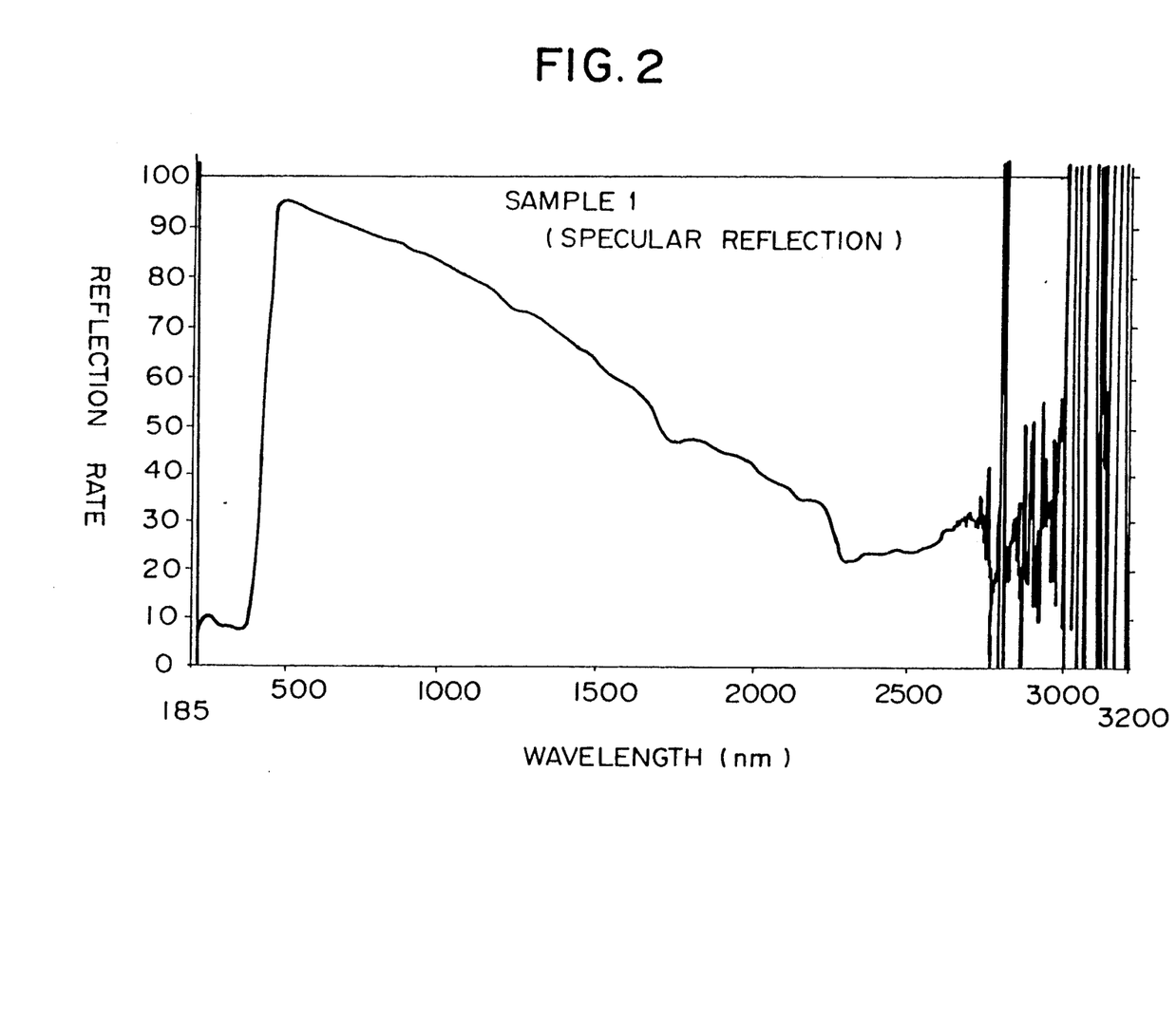
Figure 3:
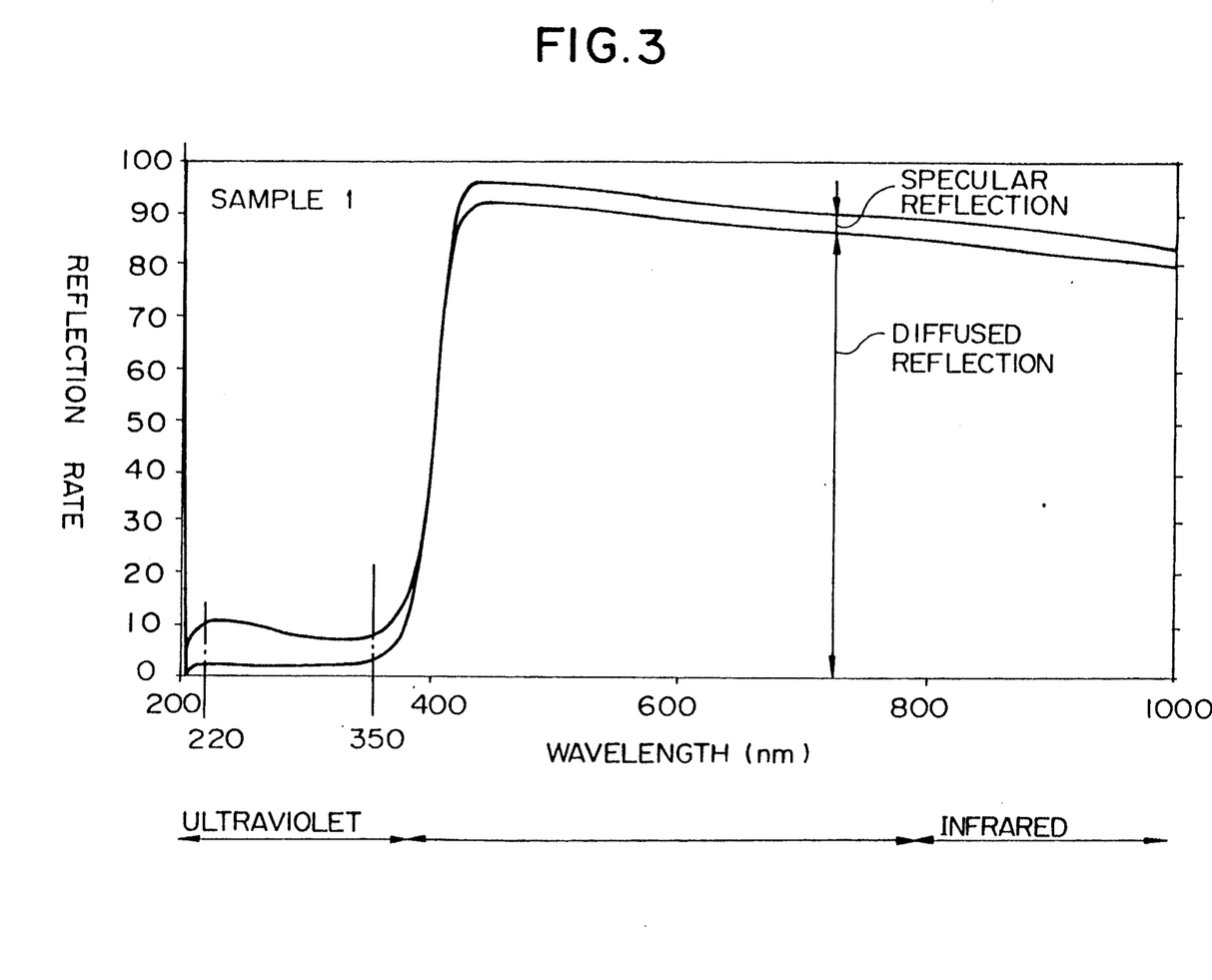

As shown in FIGS. 1, 2 and 3, when the irradiation light has a wavelength from approximately 200 nm or, more specifically, from approximately 220 nm to approximately 350 nm, which falls substantially in an ultraviolet range, the diffused reflection is very low. However, when the wavelength increases up to the visible range, the diffused reflection is remarkably increased.

Figure 4:
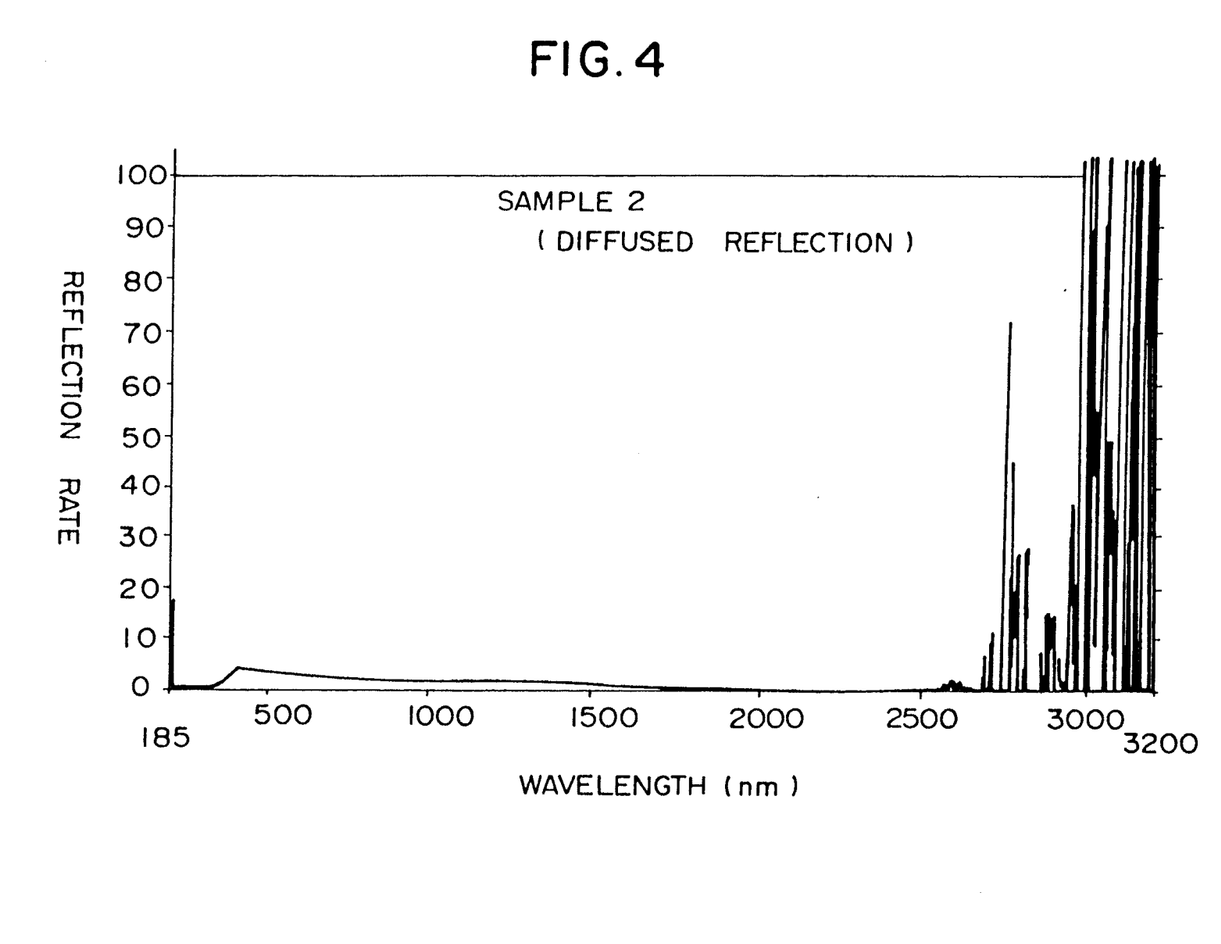
Figure 5:
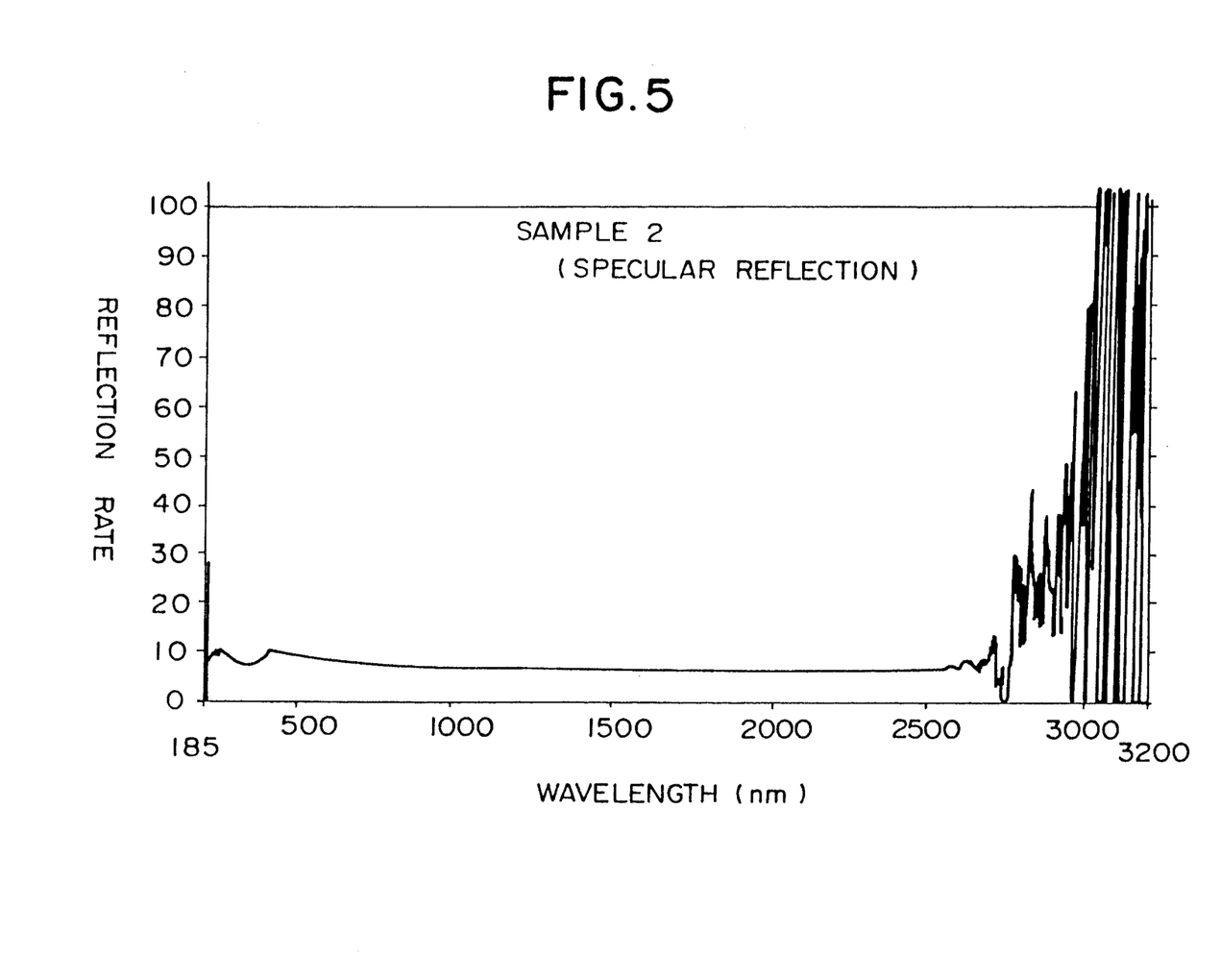
Figure 6:
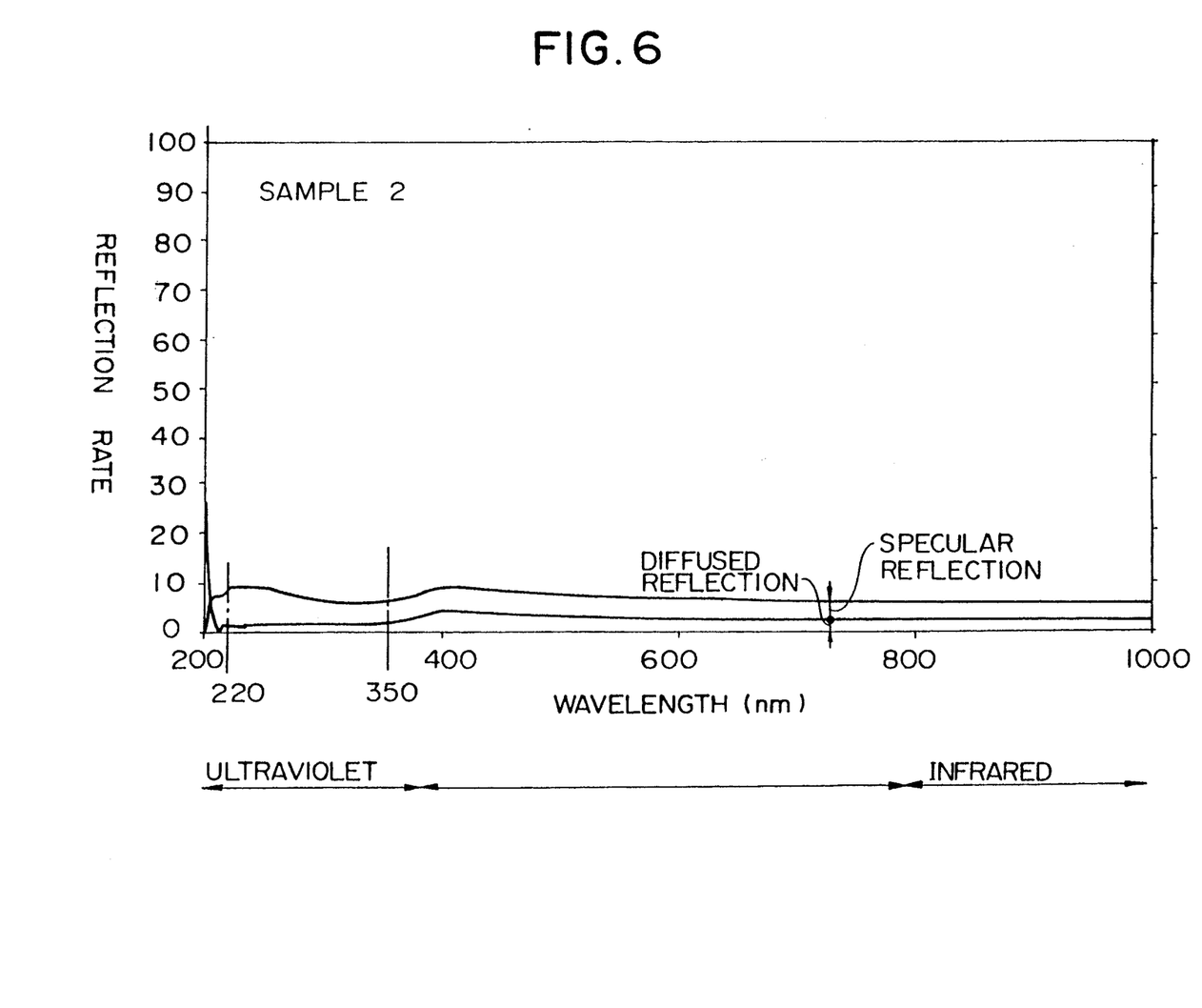

As shown in FIGS. 4, 5 and 6, with regard to sample 2, there is no substantial diffused reflection for wavelengths of approximately 200 nm–350 nm or, more specifically, 220 nm–350nm. The diffused reflection is produced in the visible light range as with sample 1. However, the level of the diffused reflection is remarkably reduced relative to sample 1.

Figure 7:
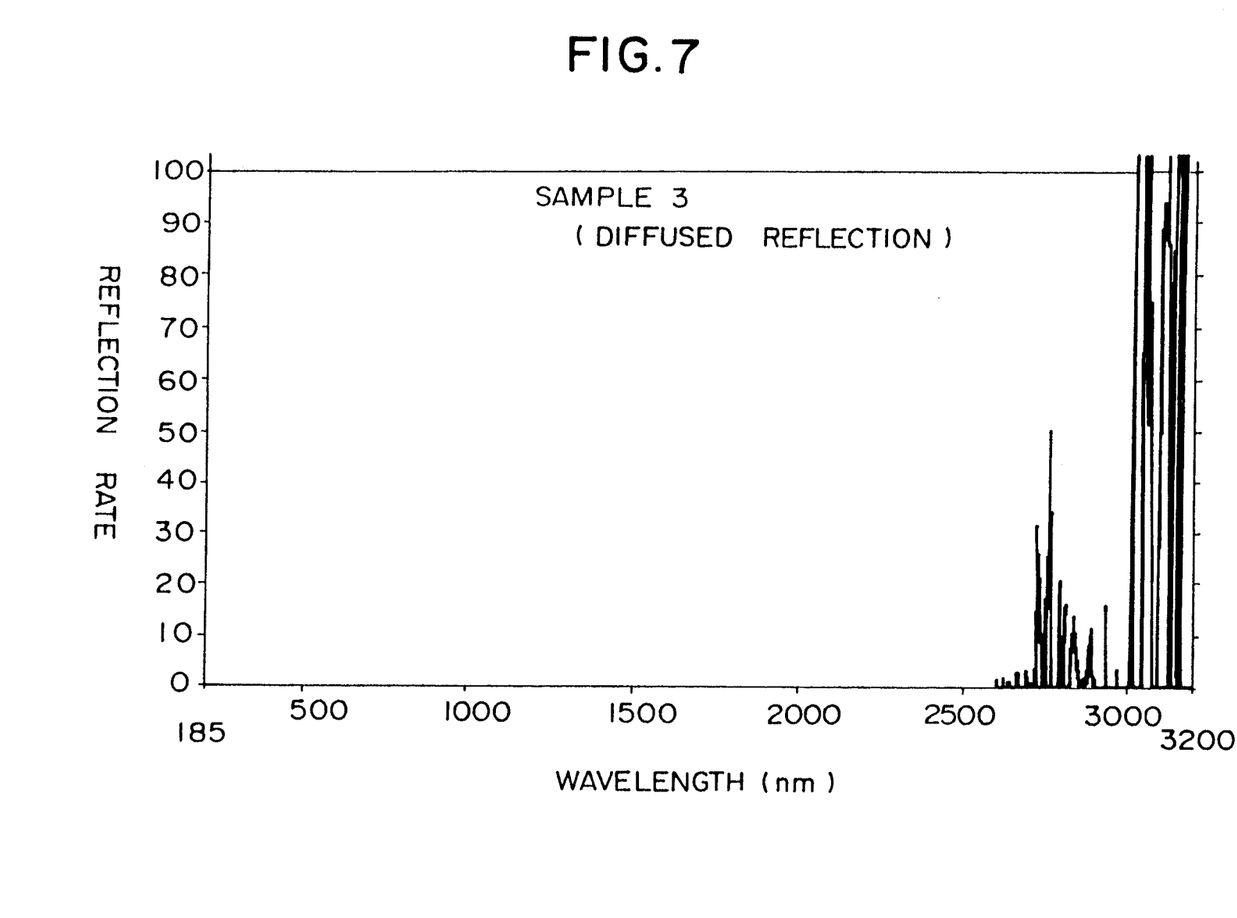
Figure 8:
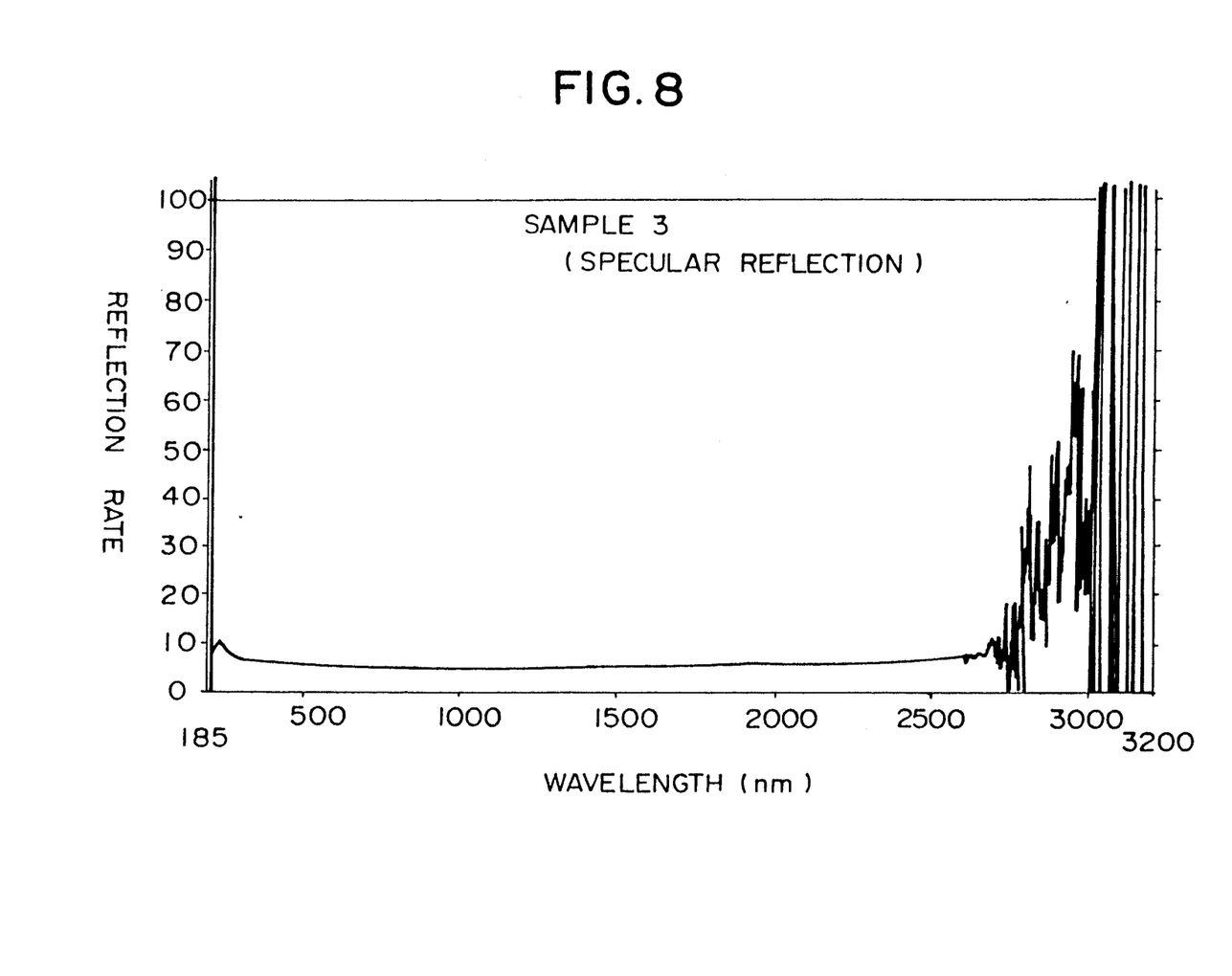

According to FIGS. 7 and 8, with regard to sample 3, there is no substantial diffused reflection throughout the whole wavelength spectrum. Accordingly, samples 2 and 3 produce less diffused reflection as compared to sample 1 because the carbon black as a pigment is contained in samples 2 and 3 as opposed to sample 1.

From the above result of the reflection rate experiment, it is derived that irradiation light of 200 nm to 350 nm in wavelength and, more specifically, from 220 nm to 350 nm in wavelength, can be effectively utilized for accurate detection of flaws in the coating irrespective of the color thereof. As the inclusion of the carbon black is increased, the diffused reflection is reduced. However, since the specular reflection is also reduced, the ratio of the diffused reflection to the specular reflection is increased. As a result, even if the inclusion of the carbon black is increased and the diffused reflection is reduced, the light having a wavelength ranging from approximately 200 nm to 350 nm is preferable for accomplishing accurate detection of the flaws in the coating. In particular, if a camera, as an imaging device, utilizes only the light having a wavelength from 200 nm to 350 nm in forming the image, the influence of the diffused reflection can be avoided. For this purpose, the irradiation device may irradiate a light with a wavelength from 220 to 350 nm onto the coating surface to be inspected. Alternatively, the imaging device may accept only reflected light having a wavelength from 220 nm to 350 nm.

Figure 9:
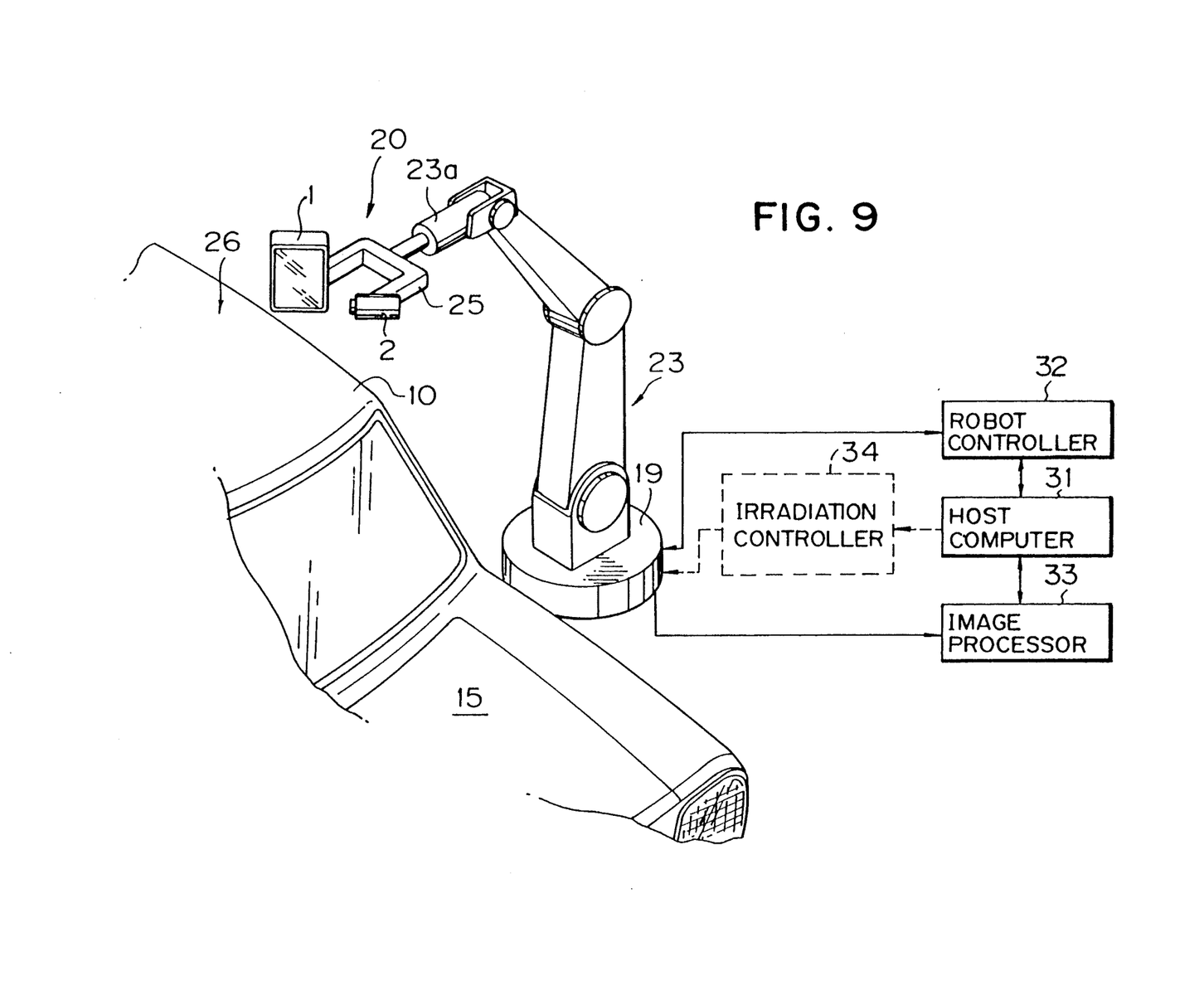
FIG. 9 is a perspective view of an apparatus including an inspection device according to the present invention.
Figure 10:
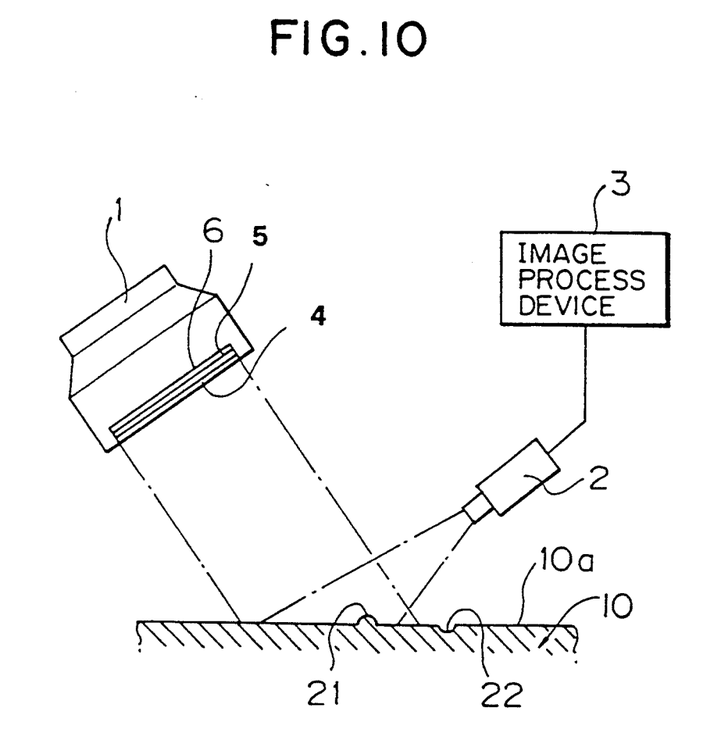
FIG. 10 is a conceptual view of the inspection device of FIG. 9.

Referring to FIGS. 9 and 10, there is shown an inspection device for inspecting a surface 10a of a coating 10 of a vehicle body and for detecting flaws thereof. The device 20 is mounted on the robot 23 which is installed on a base 19. Specifically, the device 20 is mounted on a distal end arm 23a which is provided at a top end portion of the robot 23. The inspecting device 20 is disposed so as to face a coating 10 of the roof 26 of the vehicle 15. The device 20 is provided with a light source 1, as a light irradiation device, on one arm end of support member 25 and a camera 2 on the other arm end of the support member 25 as an imaging device for receiving reflected light from the coating surface 10a and forming an image. An image processing device 3 is also provided for processing the image formed by the camera 2 to detect flaws such as scratches, pores and the like in the coating surface 10a.

The light source 1 includes an ultraviolet lamp (not shown), band pass filter 6, brightness control filter 4 and diffuse filter 5. The band pass filter 6 allows an irradiation light having a wavelength from 220 nm to 350 nm from the lamp to pass therethrough. The brightness control filter 4 provides the irradiation light with a brightness distribution having a predetermined pattern. The diffuse filter 5 scatters or diffuses the light through the brightness control filter 4 to provide a homogenized brightness on the coating surface 10a, eliminating a photometric variation within the irradiation area among the lamps. The filters 4, 5 and 6 are made from a material, such as crystal, which is resistant to ultraviolet light. A host computer 31 controls the whole apparatus including the robot 23 and the inspection device 20. For controlling the light source 1, there is provided irradiation controller 34 which receives a signal from the host computer 31. The robot 23 is controlled by a robot controller 32 which is connected with the host computer 31. In order to control the image processing device 3, there is an image processor 33 which produces a signal to the host computer 31.

In inspecting the coating surface 10a, the light source 1 and camera 2 are moved together along the coating surface 10a with a predetermined distance kept therebetween. The camera 2 receives the light reflected by the coating surface 10a, forming a substantial specular surface, which moves in one direction as the light source 1 moves, with a predetermined photometric distribution. The camera forms an image of which brightness is uniformly changed in the direction corresponding to the photometric distribution. If there are flaws 21, 22 on the coating surface 10a, the direction of the specular reflection of light is changed at the positions of flaws 21, 22 to produce a difference in brightness. This image, with a partial brightness difference, moves as the light source 1 and camera 2 move. The camera 2 produces a video signal which changes in accordance with the change of the image. The video signal is introduced into the image processing device 3. The image processing device 3 detects the size and location of the flaw based on the video signal from the camera 2.

In this embodiment, the wavelength of the irradiation light which is irradiated onto the coating surface 10a is limited so that it is in a range of 220 nm–350 nm which does not produce the substantially diffused reflection. Thus, the camera 2 forms the image based on only the specular reflection light. As a result, the image is clear so that the flaws on the coating surface 10a are clearly projected as a clear change in brightness in the image. Consequently, the flaws on the coating can be detected with a high accuracy irrespective of the color of the coating surface.

In the above embodiment, the light source 1 is provided with the band pass filter 6 which allows only light having a wavelength ranging from 220 nm to 350 nm to pass.

In another embodiment, the light source 1 irradiates a light including the visible light. The camera 2 is provided with the band pass filter 6, which allows the predetermined wave range to pass therethrough in the direction of the reflected light.

The inspecting method and device of the present invention can be applied to a coating surface which includes a sheen substance as well as a coating surface which does not include the sheen substance. It should, however, be noted that it is necessary for the reflection light to be absorbed within the coating when the present invention is applied to a coating including the sheen substance. For this reason, it is desirable for the coating to include a pigment with light absorption characteristics, such as carbon black and Chinese white, sufficient to absorb the light.

Although the present invention has been explained with reference to a specific, preferred embodiment, one of ordinary skill in the art will recognize that modifications and improvements can be made while remaining within the scope and spirit of the present invention. The scope of the present invention is determined solely by the appended claims.

What is claimed is:

1. An inspection method comprising the steps of:
    irradiating light having a predetermined changing pattern onto a substantially specular surface to be inspected by an irradiation device facing the surface,
    forming an image based on reflected light in correspondence with the predetermined changing pattern by means of an imaging device, and
    utilizing reflected light of 200-350 nm wavelength only to form the image so as to detect a flaw in the surface by identifying points which differ from the predetermined changing pattern of the light.

2. An inspection method as recited in claim 1 wherein the surface is a coating surface of a vehicle body.

3. An inspection device comprising:
    irradiation means for irradiating light having a predetermined changing pattern onto a substantially specular surface to be inspected,
    image forming means for forming an image in correspondence with the predetermined changing pattern irradiated by the irradiation means based on reflected light within a wavelength of 200-350 nm only, and
    image processing means for detecting a flaw on the surface based on the image formed by the image forming means.

4. An inspection device as recited in claim 3 wherein the irradiation means irradiates light having a wavelength of 220 nm-350 nm onto the surface.

5. An inspection device as recited in claim 3 wherein the image forming means receives light having a wavelength of 220 nm-350 nm only.

* * * * *